United States Patent [19]

Bowman

[11] 3,954,979

[45] May 4, 1976

[54] PROCESS FOR PREPARING STABILIZED YEAST AND COMPOSITIONS AND TABLETING COMPOSITION AND METHOD

[75] Inventor: Benton O. Bowman, Barrington, Ill.

[73] Assignee: Ceres Products Company, Inc., Holland, Mich.

[22] Filed: Nov. 18, 1974

[21] Appl. No.: 524,854

Related U.S. Application Data

[63] Continuation of Ser. No. 309,158, Nov. 24, 1972, abandoned.

[52] U.S. Cl. .............................. 424/195; 424/252; 424/255; 424/256
[51] Int. Cl.² ....................................... A61K 35/78
[58] Field of Search .......... 424/195, 252, 255, 266; 309/158

[56] References Cited
UNITED STATES PATENTS

| 2,322,270 | 6/1943  | Atkins et al. | 424/255 |
| 2,477,491 | 7/1949  | Miller        | 424/255 |
| 2,480,738 | 9/1949  | Jeffreys      | 424/255 |
| 3,011,944 | 12/1961 | Yamashita     | 424/252 |
| 3,116,204 | 12/1963 | Siegel et al. | 424/255 |
| 3,446,899 | 5/1969  | Cavalli et al.| 424/255 |

OTHER PUBLICATIONS

The Dispensatory of The U.S.A., 24th Ed., (1947), pp. 30–35, 737–744, 984–987, 1177–1178, 1207–1212, 1234–1235 and 1289.
Kelly et al., Brit. J. of Addiction, Jan. 1971, pp. 19–30.

*Primary Examiner*—Stanley J. Friedman
*Attorney, Agent, or Firm*—Neuman, Williams, Anderson & Olson

[57] ABSTRACT

Improved stability and high activity of certain compositions containing as essential ingredients the vitamins thiamine, riboflavin and niacin and an edible yeast which are useful in counteracting the toxic and intoxicating effects of alcohol consumption, is obtained by incorporating the vitamins, together with a vegetable gum, in a yeast cream, followed by dehydration under controlled temperature conditions. The dehydrated yeast compositions may be mixed with selected nonreactive diluents (excipients) and tableted without the use of added binders to provide a stable composition in tablet form.

10 Claims, No Drawings

PROCESS FOR PREPARING STABILIZED YEAST AND COMPOSITIONS AND TABLETING COMPOSITION AND METHOD

This is a continuation of application Ser. No. 309,158, filed Nov. 24, 1972, now abandoned.

CROSS REFERENCE TO RELATED APPLICATIONS

This application is directed to improvements in the processes and products described in co-pending application of Upham, et al., Ser. No. 279,338, filed Aug. 10, 1972, now abandoned.

BACKGROUND OF THE INVENTION

1. Field of the Invention

This invention relates to improved processes for providing stabilized compositions of the vitamins thiamine, riboflavin and niacin with edible yeast, which compositions are useful in reducing and counteracting the undesirable effects of alcohol consumption.

2. Description of the Prior Art

Various nostrums for the intoxicating effects of alcohol, particularly when consumed in excessive quantities, have been promoted mostly by word of mouth, and while too numerous to recount, it can be said that they have ranged from the consumption of strong, black coffee to inhaling pure oxygen. To date, the best information available suggests that the observable symptoms associated with intoxication are consistantly reduced and finally eliminated by normal metabolic processes over a period of time. The time required to metabolize blood stream alcohol will vary from one individual to another and is dependent on the person's metabolic rate, the amount of alcohol consumed and the body mass of the subject. Generally, speaking, a person is judged to be sober on the basis of observable motor control and recently on the basis of some studies when blood alcohol is reduced to below a particular level in terms of percent, say 0.1%. This value is somewhat arbitrary, but is the bais for the use of Breathalyzer data by law enforcement authorities to determine whether a person has sufficient alcohol in his blood stream to be regarded as presumptively or legally intoxicated. Unfortunately, this presumption is based on a correlation between bloodstream alcohol and an assumed lack of motor control or judgment and is not necessarily accurate.

The co-pending application of Upham, et al., identified above, discloses that compositions containing as essential components the vitamins thiamine, riboflavin and niacin preferably in conjunction with edible yeast at appropriate dosage concentrations, may be employed to reduce the observable intoxicating effects or symptoms of alcohol ingestion, or more particularly, the effects known as inebriation at rates considerably more rapid than normal metabolism or unaided time dependent sobering. In other words, the compositions, when ingested by a subject who has consumed an excess of alcohol, produces an observable sobering effect.

It should be understood that the sobering phenomenon and observable regain of motor control obtained by the use of these compositions cannot be explained in terms of metabolism of blood alcohol, but apparently rests on some other basis. The co-pending Upham, et a. application teaches that stability of the compositions is a problem in the sense that the composition loses its efficacy in producing the desired sobering effect when exposed to excessive heat, light or moisture and when compounded with certain conventional diluents or tableting aids.

These stability problems become especially significant in that the composition must be formulated in a manner for consumer use that will be both convenient and palatable.

It has been found that these compositions in the powder form are not generally regarded as palatable, even when mixed with masking liquids such as orange juice or tomato juice. Generally, the unpalatability of a product may be minimized to some degree by tableting so that the person ingesting or swallowing the same does not experience a highly undesirable taste in view of the fact that the products in tablet form have a short residence time in the mouth.

It has been found, however, that normal tableting procedures employing binders, excipients or diluents have not been satisfactory from the point of view of maintaining the efficacy of the composition. Conventional tableting procedures require the preparation of a granulation which is a powdered or granulated admixture of the active ingredients of a tablet, a binder material, usually some moisture, and excipients (diluents). Following these conventional tablet forming procedures with the compositions of the present invention, containing the above-noted active ingredients, produces a product in which the desired activity is markedly reduced. For example, binders such as gelatin, carrageenin and polyvinylpyrrolidine and excipients such as talc, chalk, silicates, bicarbonates, calcium carbonate, dicalcium and tricalcium phosphates and the like, and multipurpose additives such as fatty acid salts or esters, when employed with these compositions containing the noted essential components in conventional tableting procedures, either do not produce satisfactory tablets or more commonly produce tablets which do not have the desired ameliorative effect when ingested by a subject who has consumed alcohol, so as to produce toxic or intoxicating symptoms. Another difficulty with the typical granulation process is that the introduction of moisture requires a drying step in which th presence of certain binders and moisture tends to reduce the activity of the compounds. This activity reduction does not appear to be a chemical change since analysis of the products shows the vitamins and yeast are present in essentially the originally calculated amounts. Thus, the inactivation or inhibiting effect is subtle and not readily explainable from the point of view of ordinary chemical reaction or degradation and, indeed, insofar as information is available, it does not appear that the vitamins and yeast products have been damaged or deteriorated from the point of view of their normal functions as vitamins or nutritional materials, but the essential components of the composition no longer efficaciously and constantly reduce the observable effects of alcohol in a subject's system.

Other common alternatives to masking unpalatability in orally ingested compositions include the use of coatings on pills or tablets or the use of gelatin capsules. These alternatives, however, suffer from drawbakcs, namely, the coating or gelatin capsule introduces a time delay factor since the coating or capsule must dissolve before the active ingredients are available to the digestive system and can enter the blood stream of the subject. The purpose of a sobering-up composition is to provide a rapid sobering effect in the subject and to the extent that this is delayed, this objective is obviated.

SUMMARY OF THE INVENTION

The present invention relates to a process for preparing a yeast and vitamin composition which is suitable for addition to certain diluents to form a granulation which may be tableted without the use of added moisture, heat and certain conventional tableting aids.

The process in one broad form comprises:
a. forming a uniform admixture of aqueous yeast cream, nonreactive vegetable gum binder, and the vitamins thiamine, riboflavin and niacin; and
b. dehydrating the admixture under conditions which reduce the moisture content but do not inactivate the enzymes in the yeast or the vitamin components.

The invention also broadly relates to a method of forming a relatively stable tableted composition for oral administration to ameliorate and reduce the intoxication symptoms of a subject that exhibits the symptoms of alcohol intoxication and which tablet contains as active components a composition consisting essentially of thiamine, riboflavin, niacin and yeast, said process comprising:
a. forming a uniform admixture of edible yeast cream, a nonreactive vegetable gum binder, and the vitamins thiamine, riboflavin and niacin;
b. dehydrating the admixture under conditions which reduce the moisture content but do not inactivate the enzymes of the yeast component or the vitamins;
c. grinding the dehydrated product under low temperature conditions to produce a uniform granular product;
d. admixing the granular dried product with a diluent selected from the group consisting essentially of starch, microcrystalline cellulose and mixtures thereof, in the absence of heat and moisture to form a tableting blend; and
e. forming said dry blend into tablets.

The yeast employed in the process of this invention is derived from edible yeasts such as *Saccharomyces cerevisiae* or so-called baker's yeast, as well as other commercial yeast products known by the names *Canada utilis*, *S. uvarum* (Brewers yeast), including creams made from yeast autolyzates which include water soluble cell components and solid yeast cell walls.

The yeast is in the form of so-called yeast cream which is an aqueous suspension of yeast cells. The yeast cream has varying solids contents but generally for purposes of this invention has a solids content of from about 10 to about 22 or 23%, preferably from 15 to 18%. Prior to use, the yeast as produced may be preferably debittered by washing and filtration.

The yeast cream-vitamin-vegetable gum admixture is formed by a simple mixing process, but to obtain a uniform product it is necessary to continue agitation of the mix of assure a homogeneous blend. The resulting admixture is pasteurized by heating either before addition of vitamins and/or vegetable gum or after the latter sequence being preferred since contamination by the additives is thereby minimized or counteracted.

The pasteurization step has an additional purpose, namely, to kill the yeast cells. The temperatures and times employed should not be so long as to inactivate the enzymes in the yeast or damage or modify the vitamin components. It has been found that under these high moisture conditions, the pasteurization and killing of the yeast can be accomplished by heating at temperatures between about 180° and 212°F. for brief periods of time, say 20 minutes to 2 hours, preferably between 20 and 30 minutes to avoid any possible inactivation. The yeast cells may also be killed by the addition of solvents such as toluene, acetone or chloroform, but this procedure is not preferred since the solvents represent a disposal and removal problem in normal plant operations.

The vegetable gum binder material added to the yeast cream admixture may be broadly defined as a nonreactive, non-inactivating vegetable gum binder. By the terms "nonreactive" and "non-inactivating" it is intended to exclude those typical binders such as alginates, carrigeenins, sugars, polyvinylpyrrolidine, fatty acid derivatives and the like, which have a deleterious inactivating effect on these compositions insofar as their capacity in reducing the observable effects of alcohol ingestion is concerned.

The gums found useful in this invention include the preferred gum acacia, as well as guar gum, gum tragacanth, locust bean gum and "karaya".

The diluents and excipients employed in the formation of tableting blends used in the manufacture of tablets are selected from the group consisting of starch such as corn or potato starch, microcrystalline cellulose and mixtures thereof. These materials, particularly mixtures of starch and microcrystalline cellulose in ratios form 20:80 to 80:20 are preferred; other additives can be employed which do not inactivate the enzymes in the yeast or the vitamins. The vitamins used and required in the yeast composition are thiamine (Vitamin $B_1$, as the hydrochloride or mononitrate); riboflavin (Vitamin $B_2$); and niacin (nicotinic acid), the anti-pellegra vitamin. These are incorporated into the compositions so as to produce a final tablet which contains at least 30 mg. of thiamine, 30 mg. of riboflavin, at least 10 mg. of niacin, and at least 200 to 300 mg. of yeast (dry basis). a typical dosage unit for a 150-pound man of the tableted product is about four tablets or four times the amounts indicated for each of the vitamins and yeast for a single tablet. A dosage unit, however, may vary from 40 to 200 mg. of each of the vitamins thiamine and niacin and from 10 to 80 mg., preferably from 10 to 45 mg., niacin and at least 300 mg. of yeast, preferably 800 to 1600 mg. or more of yeast (dry basis). No great benefit is achieved in employing amounts of over 200 mg. for each vitamin in a dosage unit. The dosage unit form also includes as required elements microcrystalline cellulose and starch in amounts of from 200 to 800 mg. microcrystalline cellulose and from 200 to 800 mg. of starch. Vegetable gum is also present in amounts of from 10 to 50 mg. in the dosage unit.

Care must be taken in all stages of the manufacturing and tableting process since it has been found that heat, for extended periods, say above 120°F. for 2 hours, particularly in the presence of moisture an oxygen, will also produce inactivation of the tableted product.

The tableted product should be packaged in encasements which are resistant to the transmission of moisture and air, particularly oxygen, and should be of a non-light transmitting material since these alone, particularly in conjunction with heat, act deliteriously to reduce the activity of the product for the use intended. The tablets are therefore preferably packaged in sealed flexible packaging material such as laminates of polyethylene-aluminum foil and cellophane (waterproof or saran coated preferred) or laminates of polyethylene, foil and paper or saran, polyethylene, foil and paper, in which the paper and cellophane serve as printable packaging materials.

Accordingly, one important object of the present invention is the provision of a process for preparing a composition consisting essentially of thiamine, riboflavin, niacin and edible yeast for use in countering the observable effects of alcohol consumption, which process does not inactivate the essential components and is both efficient and economical.

A further object of the invention is to provide a process for tableting said compositions which does not require a wet granulation or drying step and produces a tableted product in which the activity of the essential components is not impaired insofar as their intended use as an ameliorating agent in reducing the intoxication symptoms in subjects who have ingested or consumed alcohol.

A further object is the provision of tablets containing the active materials which are readily ingestible by the majority of users but will disintegrate relatively rapidly and become metabolically available to the subject after ingestion.

A still further object is the provision of tablets and tablet formulations which, after ingesting, will produce an observable sobering effect in most subjects in a period of less than 60 minutes.

A still further object is the provision of novel stabilized vitamin and yeast products produced by said process in pulverulent or tablet form which do not exhibit degradation on storage for prolonged periods under ordinary conditions and to dosage unit forms of these stabilized tabular products as such or in protective encasements or enwrapments.

DESCRIPTION OF THE PREFERRED EMBODIMENTS

EXAMPLE I

Part A - Premix

A premix was prepared from the following components in the proportions indicated:

|  | Parts |
|---|---|
| Thiamine (B₁) | 38.6 |
| Riboflavin (B₂) | 38.6 |
| Niacin | 12.8 |
| Gum Acacia (Spray Dried) | 10.0 |

Part B - Yeast Compositions

One hundred eighty-nine pounds of the premix prepared above was added to a washed, debittered and centrifuged yeast slurry or cream containing 500 pounds (dry basis) of yeast (*S. cerevisiae*), at a solids content of 15 to 18% and the mixture agitated for one-half hour and pasteurized by heating 15 to 20 minutes at 180°F. in a preheater. The pasteurized yeast cream is poured in the nip of a double drum drier having a drum surface temperature of 390°–400°F. with the drums rotating at 2 RPM. The paper thin film of yeast is carried on the drum surface for about 10–15 seconds and is removed from the drum as a dry, low moisture (less than 8%) product by a scraper or doctor blade and then rapidly cooled.

The flake product passes by screw or other conveyer to a Fitzmill milling machine set to produce a granular product averaging about 16 mesh. This product may be used as is or may be employed to make the more convenient tablet form.

Part C - Tableting Blend

The granulated dried vitamin and yeast composition prepared in B above was admixed with the excipients or diluents corn starch and microcrystalline cellulose to prepare a blend for tableting and in the following indicated proportions.

| Dried yeast and vitamin blend (B) | 2130 grams |
|---|---|
| Corn starch (STA-RX-1500) | 591 grams |
| Microcrystalline Cellulose (Avicel) | 120 grams |

Part D - Tableting Procedure

This tableting blend prepared in Part C was fed through a tableting machine to form 475 mg. tablets having a hardness of 6 kg., a friability of 0.55, thickness of 0.222 in., and a disintegration time of 10 minutes.

The product analyzed:

| Thiamine HCl | 38.8 mg./tablet |
|---|---|
| Riboflavin | 40.3 mg./tablet |
| Niacin | 12.4 mg./tablet |

Part E - Packaging

Tablets prepared in accordance with Part "D" above were packaged in pouches, 4 tablets to a pouch. The pouch packaging material was formed from a laminate of polyethylene, aluminum foil and reverse printed waterproof cellophane. The package pouch after filling was heat sealed.

Tests of the packaged product indicated that storage at 120°F. for 90 days did not reduce the efficacy of the tableted compositions as an ameliorative for intoxication.

EXAMPLE II

TABLETS

Other tablet products were prepared from the dry yeast product of Part B of Example I.

| Dried yeast and vitamin blend (Part B, Ex. I) | 1065 gm. |
|---|---|
| Microcrystalline Cellulose (Avicel) | 100 gm. |
| Corn Starch (STA-RX-1500) | 20 gm. |

This tablet blend was formed into 475 (average) mg. tablets, having a hardness of 7, friability of 0.33% and thickness of 0.220 inch. They had a disintegration time of 12 to 15 minutes.

EXAMPLE III

TABLETS

A similar tablet was prepared as described in Example II employing:

| Yeast Vitamin Blend (B) | 1065 |
|---|---|
| Microcrystalline Cellulose | 60 |
| Corn Starch | 295 |

The tablets had a disintegration time of 10 minutes.

The tableted products prepared in Example I were tested to determine the efficacy of the compositions in reducing the observable symptoms of intoxication in 8 volunteer subjects with the results shown in the following table. The alcohol consumed by the subjects was average 86 proof consumed in a maximum of 30 minutes. The amount ingested was calculated to produce a 0.10% alcohol blood level in the subject. The evaluation of the test subjects was by trained observer who evaluated the subject by observing, writing, drawing, speech, motor coordination, etc. The tablets were administered with a glass of water, 4 tablets per person, within 15 minutes after cessation of drinking. Vision tests were by Bausch & Lomb Orthorater.

3. A process according to claim 2 wherein the vegetable gum is gum acacia.

4. A process according to claim 2 wherein the solids content of the yeast cream is between about 15 and 18%.

5. A process according to claim 2 wherein the slurry admixture of yeast and vitamins is pasteurized at temperatures and for times that will not impair the activity of the final product prior to drying.

6. A process according to claim 2 wherein the yeast cream is debittered prior to admixture with the vitamins.

TABLE I

| SUBJECT | SEX | BODY WT. LBS. | AMOUNT ALCOHOL cc/oz. | TIME OF FIRST EFFECTS (Minutes) | TIME OF CONTROL EFFECTS (Minutes) | REMARKS |
|---|---|---|---|---|---|---|
| A | M | 180 | 210/7 | 20 | 40 | Normal |
| B | M | 145 | 210/7 | 16 | 32 | Almost completely normal in 50 minutes |
| C | M | 150 | 180/6 | 15 | 30–55 | Almost normal in 55 minutes |
| D | F | 85 | 120/4 | 28 | 28 | Sober in 62 mins. |
| E | M | 155 | 270/9 | 14 | 50 | Essentially sober in 50 mins. |
| F | M | 160 | 300/10 | 18 | 43 | Sober in 43 mins. |
| G | F | 118 | 150/5 | 22 | 49 | Essentially sober in 49 mins. |
| H | F | 110 | 150/5 | 25 | 53 | Essentially sober in 53 mins. |

What is claimed is:

1. A process for preparing a stabilized yeast and vitamin concentrate composition having high activity in reducing the observable intoxicating effects of ethyl alcohol in human subjects which comprises:
   a. admixing the vitamins thiamine, riboflavin and niacin in pre-determined ratios of 3 parts thiamine; 3 parts riboflavin; and 1 part niacin with an edible yeast cream having a yeast cell solids content of at least 10% to produce a homogeneous slurry;
   b. pasteurizing the resulting slurry; and
   c. dehydrating the slurry to reduce the moisture content to below about 8% under time and temperature conditions whereby the activity of the admixture is not impaired.

2. A process according to claim 1 for preparing a stabilized yeast and vitamin concentrate which comprises:
   a. admixing the vitamins thiamine, riboflavin and niacin and a non-inactivating vegetable gum selected from the group of gum acacia, guar gum, locust bean gum, gum tragacanth and karaya, with an edible yeast cream of Saccharamyces cerevisae, S. uvarum or Candida utilis, said cream having a yeast cell solids content of at least 10% to form a slurry;
   b. pasteurizing the yeast slurry; and
   c. dehydrating the slurry to reduce the moisture content to below 8% under time and temperature conditions whereby the activity of the admixture is not impaired and to thereby produce a granular, dry product.

7. A process for producing a tableted composition which has high activity in reducing the observable intoxicating effects of ethyl alcohol ingestion in human subjects which comprises:
   a. forming a uniform admixture of the vitamins in the ratios of 3 parts thiamine, 3 parts riboflavin and 1 part niacin, and a noninactivating vegetable gum material in an aqueous edible yeast cream;
   b. pasteurizing the admixture under time and temperature conditions that will not inactivate vitamins of the enzymes in said yeast admixture;
   c. drying the admixture under time and temperature conditions which reduce the moisture content but do not impair or inactivate the activity of the vitamins or enzymes in the yeast;
   d. comminuting the dried admixture to a uniform granular product;
   e. blending the dried granular admixture with a compound selected from a group consisting of corn starch and microcrystalline cellulose and mixtures thereof; and
   f. forming tablets from the blend which contain on a dry basis at least 30 mg. thiamine; 30 mg. riboflavin; and 10 mg. of niacin per tablet.

8. A process according to claim 7 wherein the ratio of corn starch to microcrystalline cellulose ranges from 15:85 to about 85:15.

9. A process according to claim 7 wherein the ratio of corn starch to microcrystalline cellulose ranges from 20:80 to about 80:20.

10. A process according to claim 7 wherein the tablets are packaged in moisture and air impermeable enwrapments.

* * * * *

UNITED STATES PATENT OFFICE
CERTIFICATE OF CORRECTION

PATENT NO. : 3,954,979
DATED : May 4, 1976
INVENTOR(S) : Benton O. Bowman

It is certified that error appears in the above-identified patent and that said Letters Patent are hereby corrected as shown below:

Col. 1, l. 40 - After "blood" insert -- stream --

Col. 2, l. 44 - "th" should be -- the --

Col. 2, l. 62 - "drawbakcs" should be -- drawbacks --

Col. 4, l. 39 - After the period (.) "a" should be -- A --

Col. 4, l. 58 - After "moisture", "an" should be -- and --

Signed and Sealed this

Tenth Day of August 1976

[SEAL]

Attest:

RUTH C. MASON
Attesting Officer

C. MARSHALL DANN
Commissioner of Patents and Trademarks